(12) United States Patent
Hedmann et al.

(10) Patent No.: US 8,350,195 B2
(45) Date of Patent: Jan. 8, 2013

(54) METHOD AND DEVICE FOR HEATING SOLUTIONS, PREFERABLY DIALYSIS SOLUTIONS

(75) Inventors: Frank L. Hedmann, Volkach (DE); Stephan Klatte, Nienburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 192 days.

(21) Appl. No.: 12/735,891

(22) PCT Filed: Feb. 27, 2009

(86) PCT No.: PCT/EP2009/001435
§ 371 (c)(1),
(2), (4) Date: Aug. 24, 2010

(87) PCT Pub. No.: WO2009/106354
PCT Pub. Date: Sep. 3, 2009

(65) Prior Publication Data
US 2011/0000902 A1 Jan. 6, 2011

(30) Foreign Application Priority Data
Feb. 29, 2008 (DE) .................. 10 2008 011 828

(51) Int. Cl.
*H05B 1/02* (2006.01)
(52) U.S. Cl. ........................................ 219/494
(58) Field of Classification Search ............. 219/494
See application file for complete search history.

(56) References Cited

U.S. PATENT DOCUMENTS

| | | | |
|---|---|---|---|
| 6,743,201 B1 | 6/2004 | Donig et al. | |
| 7,031,602 B2 * | 4/2006 | Faries et al. | 392/470 |
| 2004/0170409 A1 | 9/2004 | Faries, Jr. et al. | |
| 2004/0265168 A1 | 12/2004 | Bakke | |
| 2006/0195064 A1 | 8/2006 | Plahey et al. | |
| 2007/0112297 A1 | 5/2007 | Plahey et al. | |
| 2008/0058712 A1 | 3/2008 | Plahey | |
| 2008/0208111 A1 * | 8/2008 | Kamen et al. | 604/29 |

FOREIGN PATENT DOCUMENTS

| | | |
|---|---|---|
| DE | 1 122 750 B | 1/1962 |
| DE | 1 613 929 A1 | 4/1970 |
| DE | 23 60 563 A1 | 6/1975 |
| DE | 197 52 578 A1 | 6/1999 |
| EP | 0 956 876 A1 | 11/1999 |
| WO | WO 88/09186 A1 | 12/1988 |
| WO | WO 97/09074 A2 | 3/1997 |

* cited by examiner

Primary Examiner — Hoai V Ho
(74) Attorney, Agent, or Firm — Jacobson Holman PLLC

(57) ABSTRACT

A method and an apparatus for the heating of a solution, such as a dialysis solution, to a desired temperature includes heating the solution presented in a bag. The heating is effected with a heater system, which includes a heater, by means of a two-step control. The temperature forming the lower switch-on threshold of the heater and the temperature forming the upper switch-off threshold of the heater vary.

15 Claims, 2 Drawing Sheets

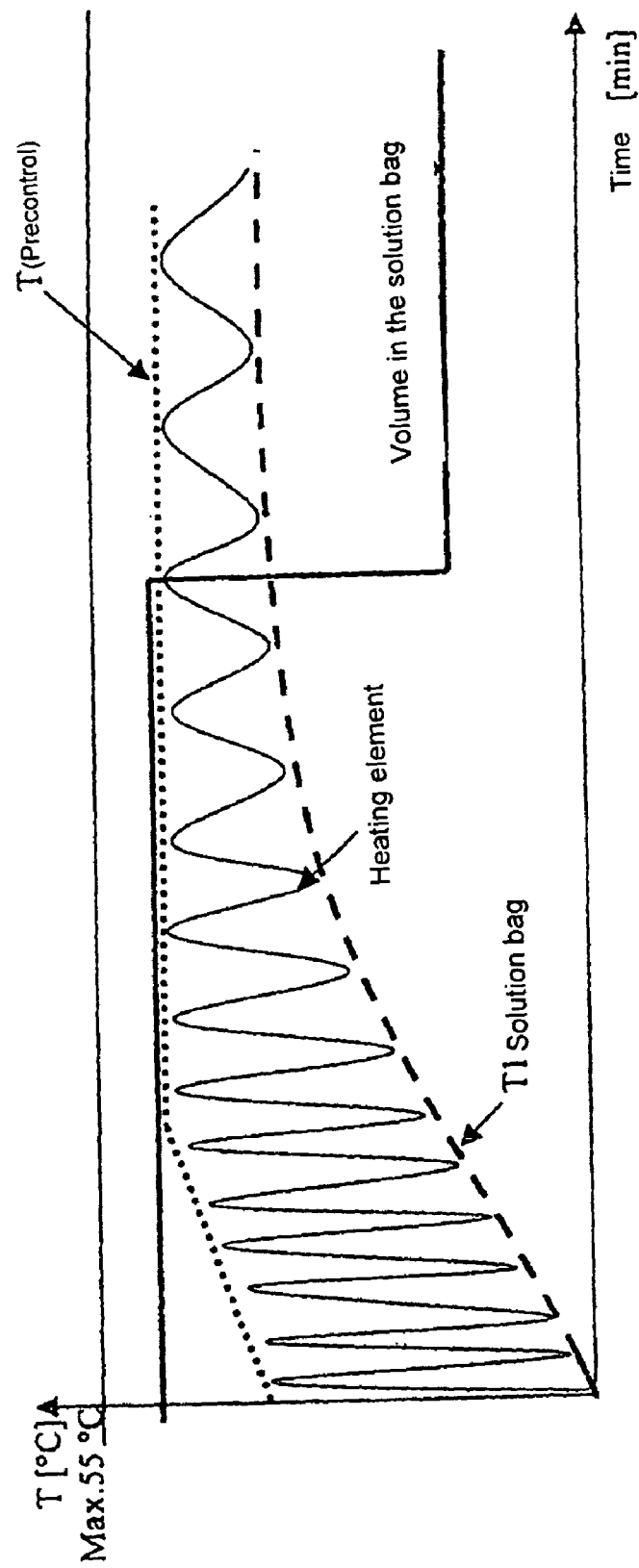

METHOD AND DEVICE FOR HEATING SOLUTIONS, PREFERABLY DIALYSIS SOLUTIONS

CROSS-REFERENCE TO RELATED APPLICATION

This is a national stage of PCT/EP09/001,435 filed Feb. 27, 2009 and published in German, which has a priority of German no. 10 2008 011 828.1 filed Feb. 29, 2008, hereby incorporated by reference.

BACKGROUND OF THE INVENTION

1. Field of Invention

The invention relates to a method for the heating of solutions, preferably dialysis solutions, as described herein.

The dialysis solutions preferably treated in accordance with the invention are used, for example, in the field of peritoneal dialysis. In peritoneal dialysis, the dialysis solution to be infused into the abdominal cavity should be approximately at body temperature. On the one hand, this is perceived as pleasant by the patient and, on the other hand, is beneficial to the health. Another application is in the area of infusion technology, blood transfusion technology or other similar areas in which the liquids have to be heated.

The invention equally relates to an apparatus, in particular in a peritoneal dialysis device, for the heating of solutions, preferably dialysis solutions, as described herein.

2. Description of the Prior Art

It is already known to achieve the temperature of dialysis solutions to be used in peritoneal dialysis before the infusion. EP 0 956 876 B1, for example, describes a cassette for the conveying of dialysis liquids in which the dialysis liquid is heated before the infusion. For this purpose, the lines conducting the dialysis liquid are arranged in spiral manner in a heatable region of the cassette.

In accordance with WO 88/09186 A1 and WO 97/09074 A2, the dialysis solution to be heated is presented in a bag and is heated in this form. In this connection, a heater serves the heating of the bag in WO 97/09074 A2.

The heating time should be minimized as much as possible during the heating of the dialysis solution. However, the starting temperature of the heater for the heating of the dialysis solution having ambient temperature cannot be selected to be at any desired level. In the case a heater is used, on the one hand, the heat stability of the dialysis solution itself and, on the other hand, the heat stability of the bag material must be taken into consideration. Furthermore, particularly for the case that the heater system is accessible to the operator, it must be configured such that a risk of injury due to burns at a correspondingly hot heater can reliably be precluded.

There is a further problem in the so-called overshooting of the heating temperature which results as follows. To achieve the fastest possible heating of the bag contents, the heating device could preferably be operated at a maximum limit temperature which takes account of the previously mentioned conditions. If, however, the bag is removed from the heater during the heating of the heater or after a corresponding reaching of the wanted desired temperature of the bag, accumulated heat arises on the heater and thereby a heat accumulation which allows the temperature to rise briefly above the permitted limit temperature. This exceeding of the limit temperature can be called overshooting. On this uncontrolled exceeding of the limit temperature, there is an acute risk of burning for the user.

SUMMARY OF THE INVENTION

It is therefore the object of the present invention to further develop a generic method and an apparatus for the heating of solutions such that a bag containing the solution can be heated to the desired end temperature as fast as possible without there being any risk of temperature overshoots on the heating of the heater.

This object is solved in accordance with the invention by the method in accordance with the feature combination as described herein. A method is accordingly proposed for the heating of solutions, preferably dialysis solutions, to a wanted desired temperature, wherein a solution presented in a bag is heated on a heater system including a heater by means of a two-step control. In accordance with the present invention, the temperature forming the upper switch-off threshold of the heater vary. The unwanted overshooting of the temperature of the heater in the heating procedure can be reliably prevented by this.

Preferred embodiments of the invention are also described herein.

In accordance with a first advantageous embodiment of the invention, the temperature $T$ of the bag containing the solution is measured by means of a first temperature sensor, whereas the temperature $T_2$ of a heating element arranged in the heater system is measured via a second temperature sensor.

A previously fixed precontrol temperature $T_V$ is advantageously used as the temperature $T_2$ forming the upper switch-off threshold. This pre-control temperature $T_V$ is determined in advance for discrete bag temperatures $T_1$.

The method in accordance with the invention is particularly advantageously carried out by means of a two-step control in which the following steps run iteratively:

measuring the temperature $T_1$ of the bag containing the solution;

setting the precontrol temperature $T_V$;

heating the heating element until the precontrol temperature $T_V$ is reached.

This method is repeated for so long until the bag has the desired temperature, with the heating element cooling down after the heating of the heating element up to the reaching of the precontrol temperature $T_V$ until it has reached the temperature the solution bag $T_1$ has reached in the meantime. Subsequently, it is heated again in each case in the following iteration steps until the reaching of the precontrol temperature $T_V$.

The precontrol temperature is preferably selected such that an overshooting of the temperature beyond the maximum heater temperature $T_{max}$ is not possible.

In accordance with a particularly advantageous embodiment of the invention, the switch-on point for the switching on of the heating element is determined in that a predetermined ratio of the temperature $T_2$ forming the upper switch-off threshold to the temperature $T_1$ of the bag containing the solution is reached.

It is in turn of particular advantage if the temperature $T_1$ of the bag containing the solution is determined when the influence of the heating element on the sensor measuring the temperature $T_1$ of the bag containing the solution has fallen below a limit value. The following phenomenon can hereby be taken into account. Since the temperature sensor for the measurement of the temperature $T_1$ is not completely thermally decoupled due to the design of the heater, the measured temperature at this sensor cannot be directly associated with the solution temperature. At the end of the heating process, the sensor for the measurement of the temperature $T_2$ adopts the temperature of the heating element, the sensor for the measurement of the temperature $T_1$ adopts a temperature which lies between the actual solution temperature and that of the heating element. In accordance with the aforesaid advantageous embodiment of the method in accordance with the invention, it is now waited until the influence of the heating element on the sensor measuring the temperature $T_1$ of the solution has fallen below a predetermined limit value. It is hereby ensured that the heat energy created is removed and has transferred into the solution so that the influence of the heating element on the sensor measuring the temperature $T_1$ is minimized and the solution temperature can now be determined with greater precision.

The aforesaid limit value can advantageously be determined in that the temperature $T_1$ of the bag containing the solution is determined from the gradient of the sensors measuring the temperatures. The gradient of the temperature changes $T_1$ and $T_2$, the gradient of the temperature change $T_1$ to $T_2$ or the temperature difference of $T_1$ and $T_2$ can advantageously be determined here.

The aforesaid object is also solved by an apparatus as described herein. Preferred embodiments of this apparatus are also described herein.

The aforesaid method and/or the aforesaid apparatus can be used in a device for peritoneal dialysis in accordance with US 2006/0195064 A1 and US 2007/0112297 A1. Reference is made to the content of US 2006/0195064 A1 and US 2007/0112297 A1 and the description of the subject matter of these documents is made the subject of the present application by reference.

BRIEF DESCRIPTION OF THE DRAWINGS

Further features, details and advantages of the invention will be explained in more detail in the following with reference to an embodiment shown in the drawing. There are shown:

FIG. 2: the temperature curve of a typical heating process entered over time in accordance with the method in accordance with the invention.

DETAILED DESCRIPTION OF THE PREFERRED EMBODIMENTS

Figure 1:
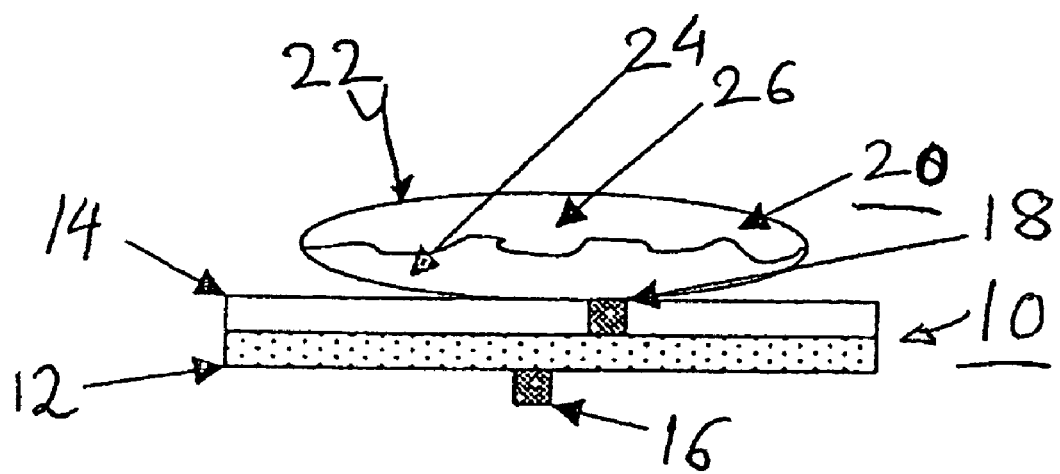
FIG. 1: a schematic representation of a heater system for the carrying out of the method in accordance with the invention.

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

A heater system 10 is shown in its schematic design in FIG. 1 such as it is used for the heating of dialysis solutions used in peritoneal dialysis. The heater system 10 consists of a heating element 12 and of a heater 14 which is placed on this and which consists, for example, of aluminum. A sensor 16, which measures the temperature $T_2$ of the heater, is associated with the heating element 12. In contrast, a sensor 18 is embedded in the heater 14 and is in contact with a bag 22 containing the dialysis solution 20 to be heated, as is shown schematically in FIG. 1. During the heating by means of the heater 14 of the dialysis solution 20 presented in the bag 22, a warm solution zone 24 is formed in the direct vicinity of the heated heater and a cold solution zone 26 is formed on the side of the bag 22 facing away from the heater 14.

The dialysis solution 20 in the bag 22 should be heated to 37° C. in as short a time as possible. To enable setup times for the peritoneal dialysis in which the dialysis liquid should be used which are as short as possible, this time period should be, for example, 45 minutes. It must now be taken into account that the filling volume 22 varies during the treatment since this bag is used for the start-up phase in the peritoneal dialysis.

The shortest possible time for the heating up to 37° C. must be achieved by means of a maximum heater temperature $T_{max}$ of 55° C. This maximum heater temperature is predetermined in that a higher temperature could result in a possible injury to the patient if he touches the heater during operation.

Due to the aforesaid properties, the exact volume of the dialysis solution bag 20 is not known as a rule. The starting temperature of the dialysis solution in the solution bag is not known as a rule, either. It must also be taken into account that the temperature sensor 18 of the bag can be influenced by the temperature of the heater carrier or of the heating element.

The aforesaid demands can be achieved by means of the method management in accordance with the invention in that only so much heat energy is always fed into the heater carrier that an overshooting beyond the maximum temperature $T_{max}$ is reliably prevented. The heating procedure of the heater 14 via the heating element 12 of the heater system 10 takes place by means of a two-step controller not shown in any more detail here, but widely known in the prior art. In accordance with the invention, in contrast to the known two-step controllers in accordance with the prior art, however, the upper switch-off threshold and also the lower switch-on threshold are varied over time. In this connection, the upper switch-off threshold is limited by a previously fixed precontrol temperature $T_V$.

The switch-on point can, in contrast, be determined in that the temperature measured using the sensor 18, namely the temperature $T_1$, is in the correct ratio with the temperature of the heating element 12 measured using the sensor 16, namely the temperature $T_2$.

The precontrol temperature is determined as follows in accordance with the embodiment shown here. To meter the amount of energy of the heating element such that no overshooting of the temperature beyond the maximum temperature $T_{max}$ arises, the precontrol temperature $T_V$ is determined in dependence on the heater temperature. It is the aim in this connection to select a precontrol temperature which allows a cold bag 20 with dialysis solution 20, containing 5 liters for example, to be removed from a still heating heater 14 without an overshooting beyond the maximum temperature $T_{max}$ taking place.

In this context, it is very easy for the heating element to give off heat energy into the solution 20 due to the large temperature drop between the heating element 14 and the bag 22. However, at that moment at which the bag is removed from the heater 14, accumulated heat arises here which can no longer be dissipated so fast to the environment. This results in the previously described overheating of the heater system 10.

To prevent this above-described heating, the precontrol temperature $T_V$ must be selected to be relatively low, on the one hand, but so high to ensure a fast heating of the solution.

In accordance with the invention, the measured solution bag temperature $T_1$ is put into a fixed ratio to the precontrol temperature $T_V$. This relationship is shown with reference to the embodiment reproduced in the following table:

| $T_1$ | $T_V$ |
|---|---|
| 5° C. | 35° C. |
| 10° C. | 37° C. |
| 15° C. | 39° C. |
| 20° C. | 41° C. |
| 25° C. | 43° C. |
| 30° C. | 45° C. |
| 35° C. | 47° C. |

The association of the values in the aforesaid table signifies that, for example on the measurement of a temperature value $T_1$ of 15° C., the predetermined precontrol temperature value $T_V$ is set to 39° C. as the upper switch-off threshold.

The course of the method in accordance with the invention can now be explained with the temperature curve shown in FIG. 2. The iterative procedure is as follows here:

In a first step, the solvent temperature $T_1$ is determined by the sensor 18. The precontrol temperature $T_V$ is selected from the above table in dependence on this measured temperature $T_1$. The heater system 10 is now heated until the heating element 12 has reached the precontrol temperature $T_V$. It is monitored via the sensor 16 and the temperature curve $T_2$ of the heating element 12.

In the next step, the solution temperature of the heated part of the solution 20 is measured and the aforesaid course of the method is repeated until the desired solvent temperature is reached.

It is not necessary in the method in accordance with the invention for the heating transition resistance between the heating element 14 and the bag 22 with the contained solution 20 to be known. Different materials can be used here, for example aluminum for the heater carrier and for example PVC for the solvent bag 22.

The contact surface of the bag on the heater carrier can vary in dependence on the bag size and the bag volume; nor does it have to be known to the system to carry out the method in accordance with the invention.

In accordance with the method in accordance with the invention, the dead time in which the generated heat energy from the heating element 12 is transferred into the solution bag 22 and has heated the solution there can also be taken into account.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of heating a solution contained in a bag to a desired temperature, comprising:
    heating the solution with a heater system having a heating element via a two-step control,
    including varying a temperature that constitutes a lower switch-on threshold of the heating element and a temperature that constitutes an upper switch-off threshold of the heating element by iteratively increasing the temperatures during the heating.

2. The method in accordance with claim 1, wherein a temperature $T_1$ of the bag containing the solution is measured via a first temperature sensor, and a temperature $T_2$ of a heating element arranged in the heater system is measured via a second temperature sensor.

3. The method in accordance with claim 1, wherein a previously fixed precontrol temperature $T_V$ is used as a temperature $T_2$ that constitutes the upper switch-off threshold.

4. The method in accordance with claim 1, wherein a precontrol temperature for a discrete bag temperature $T_1$ is determined in advance.

5. The method in accordance with claim 1, wherein the two-step control includes the following steps taking place iteratively:
    measuring a temperature $T_1$ of the bag containing the solution;
    setting a precontrol temperature $T_V$; and
    heating the heating element until the precontrol temperature $T_V$ is reached.

6. The method in accordance with claim 3, wherein the precontrol temperature is selected such that an overshooting of a temperature beyond a maximum heater temperature $T_{max}$ is not possible.

7. The method in accordance with claim 1, wherein a switch-on point for the switching on of the heating element is determined such that a predetermined ratio of a temperature $T_2$ that constitutes the upper switch-off threshold to a temperature $T_1$ of the bag containing the solution is reached.

8. The method in accordance with claim 1, wherein a temperature $T_1$ of the bag containing the solution is determined when an influence of the heating element on a sensor measuring the temperature $T_1$ has fallen below a limit value.

9. The method in accordance with claim 8, wherein the temperature $T_1$ of the bag containing the solution is determined from a gradient of the sensor measuring the temperature.

10. A heating system for heating a solution contained in a bag to a desired temperature via a two-step control by varying a temperature that constitutes a lower switch-on threshold of a heating element and a temperature that constitutes an upper switch-off threshold of the heating element by iteratively increasing the temperatures during the heating, said heating system comprising:
    an element configured to make variable the temperature that constitutes the lower switch-on threshold of the heating element and the temperature that constitutes the upper switch-on threshold of the heating element.

11. The heating system in accordance with claim 10, wherein the element that makes variable the temperatures is configured to store discrete temperature values which correspond to the temperatures that constitute the upper switch-off threshold of the heating element.

12. The heating system in accordance with claim 10, wherein a first temperature sensor is embedded in the heating element.

13. The heating system in accordance with claim 10, wherein a temperature sensor is arranged on the heating element.

14. The method according to claim 1, wherein the solution is a dialysis solution.

15. The method according to claim 1, wherein a temperature $T_1$ of the bag containing the solution is measured and is employed in a fixed ratio to a previously fixed precontrol temperature $T_V$ which constitutes the upper switch-off threshold.

* * * * *